(12) United States Patent
Thum et al.

(10) Patent No.: US 8,796,000 B2
(45) Date of Patent: *Aug. 5, 2014

(54) POLYETHERSILOXANE-COATED ENZYME PREPARATIONS

(71) Applicant: Evonik Goldschmidt GMBH, Essen (DE)

(72) Inventors: Oliver Thum, Ratingen (DE); Marion Ansorge-Schumacher, Dresden (DE); Lars Wiemann, Straubing (DE); Michael Ferenz, Essen (DE); Matthias Naumann, Hamburg, DE (US)

(73) Assignee: Evonik Degussa GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/942,131

(22) Filed: Jul. 15, 2013

(65) Prior Publication Data

US 2013/0302874 A1    Nov. 14, 2013

Related U.S. Application Data

(62) Division of application No. 12/551,975, filed on Sep. 1, 2009, now Pat. No. 8,486,677.

(51) Int. Cl.
   *C12N 11/14* (2006.01)

(52) U.S. Cl.
   USPC .................. 435/176; 435/180; 435/174

(58) Field of Classification Search
   None
   See application file for complete search history.

(56) References Cited

U.S. PATENT DOCUMENTS

| | | | |
|---|---|---|---|
| 5,494,815 | A | 2/1996 | von Gentzkow et al. |
| 7,070,963 | B2 | 7/2006 | Verseck et al. |
| 7,196,153 | B2 | 3/2007 | Burkhart et al. |
| 2006/0155089 | A1 | 7/2006 | Ferenz et al. |
| 2006/0155090 | A1 | 7/2006 | Ferenz |
| 2006/0188455 | A1 | 8/2006 | Ferenz et al. |
| 2006/0188456 | A1 | 8/2006 | Ferenz et al. |
| 2007/0059539 | A1 | 3/2007 | Doehler et al. |
| 2007/0100153 | A1 | 5/2007 | Brueckner et al. |
| 2007/0184006 | A1 | 8/2007 | Ferenz et al. |
| 2007/0287765 | A1 | 12/2007 | Busch et al. |
| 2008/0027202 | A1 | 1/2008 | Ferenz et al. |
| 2008/0064782 | A1 | 3/2008 | Doehler et al. |
| 2008/0076842 | A1 | 3/2008 | Ferenz et al. |
| 2008/0187702 | A1 | 8/2008 | Ferenz et al. |
| 2008/0305065 | A1 | 12/2008 | Ferenz et al. |
| 2009/0017519 | A1 | 1/2009 | Thum et al. |
| 2009/0030097 | A1 | 1/2009 | Knott et al. |
| 2009/0062459 | A1 | 3/2009 | Thum et al. |
| 2009/0075851 | A1 | 3/2009 | Thum et al. |
| 2009/0181439 | A1 | 7/2009 | Thum et al. |

FOREIGN PATENT DOCUMENTS

| | | |
|---|---|---|
| DE | 2800710 | 7/1979 |
| DE | 4019249 | 8/1991 |
| DE | 102007031689 | 1/2009 |
| EP | 0427088 | 5/1991 |
| EP | 0562371 | 9/1993 |
| EP | 2011865 | 1/2009 |

OTHER PUBLICATIONS

Bjorkling, F. et al., "A Highly Selective Enzyme-Catalysed Esterification of Simple Glucosides" Journal of Chem. Soc. Chem. Communication (1989) pp. 934-935.

Hoyos, P. et al., "Highly Efficient One Pot Dynamic Kinetic Resolution of Ebnzoins with Entrapped Pseudomonas Stutzeri Lipase" Journal of Molecular Catalysis B: Enzymatic (2008) pp. 133-139, vol. 52-53.

Gill, I. et al., "Bioencapsulation within Synthetic Polymers (part 2): Non-Sol-Gel Protein-Polymer Biocomposites" Trends in Biotechnology (2000) pp. 469-479, vol. 18.

European Search Report dated Feb. 5, 2010.

*Primary Examiner* — Jon P Weber
*Assistant Examiner* — Robert Yamasaki
(74) *Attorney, Agent, or Firm* — Scully, Scott, Murphy & Presser, P.C.

(57) ABSTRACT

The invention is directed to enzyme preparations which are obtainable by providing enzyme immobilizates which comprise enzymes or microorganisms comprising enzymes immobilized on an inert support with a polyethersilicone coating obtained by hydrosilylation, to a process for preparing such enzyme preparations and to the use of enzyme preparations as an industrial biocatalyst.

17 Claims, No Drawings

POLYETHERSILOXANE-COATED ENZYME PREPARATIONS

CROSS REFERENCE TO RELATED APPLICATION

This application is a divisional of U.S. patent application Ser. No. 12/551,975, filed Sep. 1, 2009, the entire content and disclosure of which is incorporated herein by reference.

FIELD OF THE INVENTION

The invention relates to enzyme preparations which are useful as biocatalysts.

BACKGROUND OF THE INVENTION

Microorganisms and isolated enzymes find wide use as a catalyst in the chemical industry or in food production. An overview is offered, for example, by: A. Liese, K. Seelbach, C. Wandrey, Industrial Biotransformations, Wiley-VCH: 2006, Weinheim, Germany.

In order to ensure economic use of such biocatalysts, some conditions have to be satisfied: the biocatalyst has to be active for a sufficiently long time under the reaction conditions, it should be readily removable after the end of the reaction and it should be reusable as often as possible. Ideally, these conditions should be satisfied for a very wide range of reaction conditions (for example temperature range, type of solvents used, pressures, etc.), in order to provide as universal as possible a catalyst.

In order to satisfy these conditions, it is typically necessary to immobilize the enzymes or microorganisms comprising the enzymes used.

Frequently, the enzymes or microorganisms comprising the enzymes are immobilized noncovalently on supports; the supports used are frequently ion exchange resins or polymer particles which possess suitable particle size distributions. Examples for this purpose are the commercial products Novozym 435, Lipozym RM IM or Lipozym TL IM from Novozymes A/S, Bagsvaerd, Denmark or Amano PS, from Amano, Japan. These examples are immobilized lipases which find wide use, since such immobilizates also exhibit industrially utilizable activities in nonaqueous systems, i.e., those which comprise only organic solvents, if any, as described, for example, in J. Chem. Soc., Chem. Comm 1989, 934-935.

Patent Application DE 10 2007 031689.7 describes the various disadvantages of presently available immobilization technologies, in particular and with regard to activity and stability.

SUMMARY OF THE INVENTION

The present invention discloses a novel class of enzyme preparations and a process for preparing them which overcome a large portion of these disadvantages. Essentially, it is stated that stable and highly active enzyme preparations can be obtained by first adsorbing enzymes or microorganisms comprising enzymes on a suitable support and then providing this immobilizate with a silicone polymer which is accessible by a hydrosilylation reaction.

The working examples of this application describe, however, as units for the hydrosilylation, in addition to SiH siloxanes of various topologies, siloxanes provided only with terminally unsaturated organic radicals.

For fine adjustment of the properties of the enzyme preparations thus obtained, it would, however, be desirable also to be able to use other units as well as siloxane chains. A person skilled in the art is aware that silicone compounds have particular properties, for example limited miscibility with other substance classes, for example many oleochemical derivatives or water.

There is therefore still a need for methods of enzyme immobilization which overcome the disadvantages of the prior art, in order to implement biocatalytic processes which have not been achievable to date.

As such, the present invention provides enzyme preparations which do not have one or more of the disadvantages of prior art preparations. More particularly, enzyme preparations which have a comparable stability and activity to enzyme preparations coated with pure silicone polymers, but simultaneously also have other structural elements, are provided.

It has been found that, surprisingly, enzyme preparations that avoid one or more drawbacks with prior art enzyme preparation can be obtained by immobilizing enzymes or microorganisms comprising enzymes on an inert support and then providing them with a polyethersiloxane coating obtained by hydrosilylating Si—H-functional polysiloxanes, the olefinic units used being polyethers bearing at least one terminally unsaturated group and, optionally additionally siloxanes which bear terminally unsaturated organic radicals, with the proviso that at least one olefinic unit which has at least two terminally unsaturated groups is present.

The present invention therefore provides enzyme preparations which are obtainable by providing enzyme immobilizates which comprise enzymes or microorganisms comprising enzymes immobilized on an inert support with a polyethersiloxane coating obtained by hydrosilylating Si—H-functional polysiloxanes using polyethers bearing at least one terminally unsaturated group, and the use thereof as an industrial biocatalyst.

The present invention also provides a process for preparing the inventive enzyme preparations, which is characterized in that enzyme immobilizates which comprise enzymes or microorganisms comprising enzymes immobilized on an inert support are provided with a polyethersiloxane coating obtained by hydrosilylating Si—H-functional polysiloxanes using polyethers bearing at least one terminally unsaturated group.

The inventive enzyme preparations have the advantage that they have a high stability with respect to mechanical forces and with respect to desorption. In spite of these improved properties, the inventive enzyme preparations have specific activities in various aqueous reaction mixtures (for example in the hydrolysis of tributyrin) and nonaqueous reaction mixtures (for example in the solvent-free synthesis of propyl laurate), which are high enough to enable industrial use.

DETAILED DESCRIPTION OF THE INVENTION

The inventive enzyme preparations and a process for preparation thereof are described below by way of example, without any intention that the invention be restricted to these illustrative embodiments. When ranges, general formulae or compound classes are specified below, these shall not only encompass the corresponding ranges or groups of compounds which are mentioned explicitly but also all sub-ranges and sub-groups of compounds which can be obtained by selecting individual values (ranges) or compounds. When documents are cited within the present description, their contents shall be incorporated completely in the disclosure-content of the present invention. When compounds, for example organically modified polysiloxanes, which may have different units more than once are described in the context of the present invention, they may occur in these compounds in random distribution (statistical oligomer) or ordered (block oligomer). Figures for the number of units in such compounds should be interpreted as the mean value, averaged over all appropriate compounds.

The inventive enzyme preparations are notable in that they are obtainable by providing enzyme immobilizates which comprise enzymes or microorganisms comprising enzymes immobilized on an inert support with a silicone coating which is obtained by hydrosilylating Si—H-functional polysiloxanes, the olefinic units used are polyethers bearing at least one terminally unsaturated group and optionally additionally siloxanes which bear terminally unsaturated organic radicals, with the proviso that at least one olefinic unit which has at least two terminally unsaturated groups is present.

To produce the enzyme immobilizates of the present invention, it is possible to use whole cells, resting cells, purified enzymes or cell extracts which comprise the corresponding enzymes, or mixtures thereof. Preference is given to using hydrolytic enzymes, for example lipases, esterases or proteases, for example lipases from *Candida rugosa*, *Candida antarctica*, *Pseudomonas* sp., *Thermomyces lanuginosus*, porcine pancreas, *Mucor miehei*, *Alcaligenes* sp., cholesterol esterase from *Candida rugosa*, and esterase from the porcine liver, more preferably lipases. Accordingly, the enzyme immobilizates of the invention preferably comprise enzymes from the class of the hydrolases, preferably lipases.

The inert supports used may be inert organic or inorganic supports. The inert supports used, or present in the enzyme immobilizate, are preferably particulate supports which have a particle size distribution in which at least 90% of the particles have a particle size of 10 to 5000 μm, preferably of 50 μm to 2000 μm. The organic supports used may be those which comprise, or consist of, polyacrylate, polymethacrylate, polyvinylstyrene, styrene-divinylbenzene copolymers, polypropylene, polyethylene, polyethylene terephthalate, PTFE and/or other polymers. The support materials used may, depending on the enzyme to be immobilized, be acidic or basic ion exchange resins, for example Duolite A568, Duolite XAD 761, Duolite XAD 1180, Duolite XAD 7HP, Amberlite IR 120, Amberlite IR 400, Amberlite CG 50, Amberlyst 15 (all products from Rohm and Haas) or Lewatit CNP 105 and Lewatit VP OC 1600 (products from Lanxess, Leverkusen, Germany). The inorganic supports used may be oxidic and/or ceramic supports known from the prior art. In particular, the inorganic supports used may, for example, be Celite, zeolites, silica, controlled-pore glass (CPG) or other supports, as described, for example, in L. Cao, "Carrier-bound Immobilized Enzymes: Principles, Application and Design", Wiley-VCH: 2005, Weinheim, Germany. More preferably, the inert supports present in the enzyme immobilizate or the inert supports used to produce the enzyme immobilizates consist of silica, polyvinylstyrene, polymethacrylate or polyacrylate.

The immobilization on the particles can, in accordance with the invention, be effected covalently or noncovalently, preferably noncovalently. For noncovalent immobilization, the support can be incubated or impregnated, for example, with an aqueous enzyme solution which may optionally comprise further constituents, for example inorganic salts or detergents. This incubation/impregnation can be carried out, for example, at temperatures between 0° C. and 50° C., preferably between 0° C. and 40° C. Preference is given to effecting the incubation/impregnation over a period of a few minutes to a few hours. The progress of the incubation can be effected by determining the concentration of the enzyme in the solution with the common methods for protein determination. On attainment of the desired degree of immobilization, the support can preferably be washed with water and, if desired, dried. An enzyme immobilizate obtained in this way can subsequently be provided with a polyethersilicone coating in accordance with the invention.

According to the invention, it is, however, also possible to use enzyme immobilizates which are commercially available, for example Novozym 435, Lipozym RM IM or Lipozym TL IM from Novozymes A/S, Bagsvaerd, Denmark, or Amano PS from Amano, Japan.

According to the invention, the polyethersiloxane coating is obtained by hydrosilylation. To this end, preference is given to reacting Si—H-functional polysiloxanes in the presence of at least one catalyst, preferably transition metal catalysts, with polyethers which bear at least one terminally unsaturated group.

The Si—H-functional polysiloxanes used are preferably Si—H polysiloxanes of the general formula (I)

$$M_a D_b D'_c T_d Q_e \quad (I)$$

where
$M = [R^1{}_2 R^{2a} SiO_{1/2}]$
$D = [R^1{}_2 SiO_{2/2}]$
$D' = [R^1 R^{2b} SiO_{2/2}]$
$T = [R^1 SiO_{3/2}]$
$Q = [SiO_{4/2}]$
$N^1 = a+b+c+d+e = 3$ to 850, preferably 6 to 160,
$a = 2$ to 10, preferably 2 to 4, especially 2,
$b = 1$ to 800, preferably 2 to 150,
$c = 0$ to 400, preferably 2 to 75,
$d = 0$ to 10, preferably 0,
$e = 0$ to 10, preferably 0,
$R^1$ are the same or different and are each independently selected from the group comprising: saturated or unsaturated, optionally branched alkyl groups having 1 to 30 carbon atoms, alkaryl radicals having 7 to 30 carbon atoms, aryl radicals having 6 to 30 carbon atoms, preferably alkyl groups having 1 to 4 carbon atoms or phenyl, especially methyl,
$R^{2a}$ is independently hydrogen or $R^1$ and
$R^{2b}$ is independently hydrogen or $R^1$.

The Si—H-functional polysiloxane used is preferably an Si—H polysiloxane of the general formula (I) where
$N^1 = a+b+c+d+e = 6$ to 160,
$a = 2$,
$b = 2$ to 150,
$c = 2$ to 75,
$d = 0$ and
$e = 0$.

It is familiar to a person skilled in the art that the compounds are present or may be present in the form of a mixture with a distribution regulated essentially by statistical laws. The values of the indices a, b, c, d and e are therefore typically mean values.

According to the invention, the polyethers bearing at least one terminally unsaturated group used are those of the general formula (II):

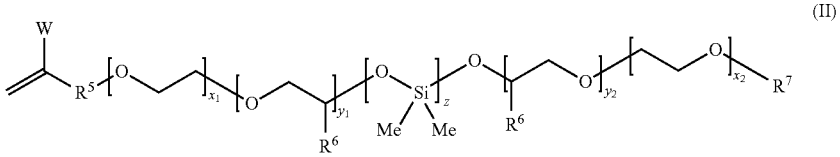

(II)

where
$N^2 = x_1+x_2+y_1+y_2 = 1$ to 500, preferably 2 to 200, especially 3 to 100,
$x_1 = 0$ to 200, preferably 1 to 200, especially 3 to 100,
$x_2 = 0$ to 100, preferably 1 to 100, especially 3 to 100,
$y_1 = 0$ to 200, preferably 1 to 200, especially 3 to 100,
$y_2 = 0$ to 100, preferably 1 to 200, especially 3 to 100,
$z = 0$ to 500, preferably 0 to 100,
W = hydrogen or methyl, preferably hydrogen,
$R^5$ is an optionally branched, optionally substituted alkylene radical which optionally bears double bonds and has 1 to 30 carbon atoms,
$R^6$ is independently a radical selected from the group comprising methyl, ethyl and phenyl, preferably methyl, and
$R^7$ is an optionally branched, optionally substituted alkyl radical or carboxyl radical which optionally contains double bonds and has 1 to 30 carbon atoms, with the proviso that, when $z=0$, $x_2=y_2=0$.

It is familiar to a person skilled in the art that the compounds are present or may be present in the form of a mixture with a distribution regulated essentially by statistical laws. The values of the indices $x_1$, $x_2$, $y_1$ and $y_2$ are therefore typically mean values.

It is preferred that a polyether of the general formula (II) is used, the polyether consisting exclusively of ethylene glycol units, i.e., $y_1=y_2=0$; equally preferably, a polyether of the general formula (II) is used, the polyether being free of ethylene glycol units, i.e., $x_1=x_2=0$.

It is additionally preferred that a polyether of the general formula (II) is used, where $x_1+x_2$ and $y_1+y_2$ are each greater than 1, more preferably are each greater than 3.

It may be advantageous when polyethers of the general formula (II) in which $z=0$ are used.

In a preferred embodiment of the use of polyethers as the olefinic reactant, a polyether of the general formula (II) where $z=0$ is used, in which
$R^5$ is an alkylene radical having 1 to 30 carbon atoms, preferably having 1 to 9 carbon atoms, more preferably having 1 to 4 carbon atoms, especially methylene, and
$R^7$ is an optionally branched, terminally unsaturated alkyl radical having 3 to 30 carbon atoms, preferably having 3 to 11 carbon atoms, more preferably having 3 to 6 carbon atoms, especially allyl or methallyl.

However, it may also be advantageous when polyethers of the general formula (II) in which $z>0$ are used.

In a preferred embodiment of the use of polyethers as the olefinic reactant, a polyether of the general formula (II) is used, where $z=1$ to 500, preferably 3 to 200, especially 6 to 100. In this embodiment, it is preferred that a polyether of the general formula (II) is used, where
$N^2 = x_1+x_2+y_1+y_2 = 2$ to 500, preferably 4 to 200, especially 6 to 100,
$R^5$ is an alkylene radical having 1 to 30 carbon atoms, preferably having 1 to 9 carbon atoms, more preferably having 1 to 4 carbon atoms, especially methylene, and
$R^7$ is an optionally branched, terminally unsaturated alkyl radical having 3 to 30 carbon atoms, preferably having 3 to 11 carbon atoms, more preferably having 3 to 6 carbon atoms, especially allyl or methallyl.

According to the invention, it is also possible to use mixtures of the polyethers which bear at least one terminally unsaturated group as the olefinic reactants.

The polysiloxanes which bear terminally unsaturated organic radicals used are preferably polysiloxanes of the general formula (III):

$$M_m D_n D'_o T_p Q_q \quad \text{(III)}$$

where
$M = [R^3_2 R^4 SiO_{1/2}]$
$D = [R^3_2 SiO_{2/2}]$
$D' = [R^3 R^4 SiO_{2/2}]$
$T = [R^3 SiO_{3/2}]$
$Q = [SiO_{4/2}]$
$N^2 = m+n+o+p+q = 3$ to 1000, preferably 10 to 600,
$m = 2$ to 10, preferably 2 to 4, especially 2,
$n = 1$ to 800, preferably 2 to 600,
$o = 0$ to 20, preferably 0 to 10, preferentially 0,
$p = 0$ to 10, preferably 0,
$q = 0$ to 10, preferably 0;
$R^3$ are the same or different and are each independently selected from the group comprising: saturated or unsaturated, optionally branched alkyl groups having 1 to 30 carbon atoms, alkaryl radicals having 7 to 30 carbon atoms, aryl radicals having 6 to 30 carbon atoms, preferably alkyl groups having 1 to 4 carbon atoms or phenyl, especially methyl, and
$R^4$ is independently a terminally unsaturated alkyl radical, preferably vinyl, or an alkoxy radical, preferably having 3 to 20 carbon atoms, or $R_3$.

The terminal polysiloxanes which bear terminally unsaturated organic radicals used are preferably polysiloxanes of the general formula (III) where
$N^2 = m+n+o+p+q = 10$ to 600,
$M = 2$,
$n = 2$ to 600,
$o = 0$,
$p = 0$,
$q = 0$ and
$R^4$ is independently a terminally unsaturated alkyl radical, preferably vinyl.

It is familiar to a person skilled in the art that the compounds of the formula (III) are present or may be present in the form of a mixture with a distribution regulated essentially by statistical laws. The values of the indices m, n, o, p and q are therefore typically mean values.

When the $R^7$ radical of the polyether used does not have a terminal double bond, compounds of the general formulae (II) and (III) are used in a molar ratio of 0.001:1 to 1:0.001, preferably of 0.05:1 to 5:1, especially of 0.05:1 to 1:1.

When the $R^7$ radical has a terminal double bond, it is also possible in accordance with the invention to use siloxanes which bear terminally unsaturated organic radicals. In this case, compounds of the general formulae (II) and (III) are used in a molar ratio of 0.001:1 to 1:0, preferably of 0.05:1 to 20:1, especially of 0.10:1 to 10:1.

In the case of use of polyethers as an olefinic reactant together with a further olefinic component of the general formula (III), preference is given to using a polyether of the general formula (II) where z=0, in which $R^5$ is an alkylene radical having 1 to 30 carbon atoms, preferably having 1 to 9 carbon atoms, more preferably having 1 to 4 carbon atoms, especially methylene, and $R^7$ is an alkyl radical having 1 to 30 carbon atoms, preferably having 1 to 9 carbon atoms, more preferably having 1 to 4 carbon atoms, especially methyl.

The hydrosilylation can be carried out by established methods in the presence of a catalyst. It is possible, for example, to use catalysts which are typically used for hydrosilylations, for example platinum, rhodium, osmium, ruthenium, palladium, iridium complexes or similar compounds or the corresponding pure elements or their derivatives immobilized on silica, alumina or activated carbon or similar support materials. Preference is given to performing the hydrosilylation in the presence of Pt catalysts such as cisplatin or Karstedt catalyst [tris(divinyltetramethyldisiloxane)bis-platinum].

The amount of catalyst used is preferably $10^{-7}$ to $10^{-1}$ mol per mole of olefin or per mole of terminal carbon-carbon double bond, preferably 1 to 100 ppm. The hydrosilylation is carried out preferably at temperatures of 0° C. to 200° C., preferably of 20° C. to 120° C.

The hydrosilylation can be carried out in the presence or absence of solvent. Generally, solvents are not needed for the performance of the reaction. The reaction can, however, be carried out in suitable solvents, for example aliphatic or aromatic hydrocarbons, cyclic oligosiloxanes, alcohols or esters. Suitable solvents are especially cyclohexane or toluene.

According to the invention, based on the mass of the support used, preferably 1 to 500% by mass, preferentially 10 to 300% by mass, more preferably 20 to 200% by mass, of siloxane and polyether components are used. The siloxane and polyether components are composed especially of the sum total of the compounds of the formulae (I), (II) and (III) and of their reaction products.

The hydrosilylation can be carried out using a wide variety of different ratios of the compounds of the formula (I) to compounds of the formula (II) or to mixtures of compounds of the formulae (II) and (III). Preference is given to effecting the hydrosilylation at a molar ratio based on the reactive groups of 1:10 to 10:1, more preferably of 1:5 to 5:1, especially preferably of 1:1.5 to 1.5:1 and most preferably of 1:13 to 1.3:1. Selection of the compounds of the general formulae (I), (II) and optionally (III) used and variation in their mixing ratios allows the properties of the polyethersilicone coating to be tailored in relation to perviousness for substrates and other reaction properties. Selection of the weight ratio of silicone components to enzyme immobilizates allows the layer thicknesses of the polyethersilicone coating to be varied and to be adjusted to appropriate requirements.

The inventive polyethersiloxane coating, produced by hydrosilylation, can be obtained by carrying out the hydrosilylation in the presence of the enzyme immobilizates. However, it is also possible that the enzyme immobilizates are provided subsequently with polyethersiloxanes obtained by hydrosilylation. This can be done, for example, by treating the enzyme immobilizates with a solution of the siloxanes and of the polyethers, for example a solution of the siloxanes and polyethers in an organic solvent, especially cyclohexane or toluene. Subsequently, the solvent can be removed, for example, by evaporation. The concentration of siloxanes and polyethers in such a solution is preferably 10 to 100% by mass, more preferably 30 to 100% by mass. However, preference is given to obtaining the inventive polyethersiloxane coating by carrying out the hydrosilylation in the presence of the enzyme immobilizates.

The inventive enzyme preparations are preferably prepared by the process according to the invention described below. This process for preparing enzyme preparations is notable in that enzyme immobilizates which comprise enzymes or microorganisms comprising enzymes immobilized on an inert support are provided with a polyethersiloxane coating obtained by hydrosilylating Si—H-functional polysiloxanes, in which the olefinic units used are polyethers bearing at least one terminally unsaturated group and optionally additionally siloxanes which bear terminally unsaturated organic radicals, with the proviso that at least one olefinic unit which has at least two terminally unsaturated groups is present.

Preference is given to performing the process according to the invention in such a way that the enzyme immobilizates are provided with a polyethersiloxane coating by contacting the enzyme immobilizates, under hydrosilylation conditions, with a reaction mixture which comprises SiH-functional polysiloxanes, polyethers bearing at least one terminally unsaturated group, and optionally polysiloxanes containing terminal carbon-carbon double bonds, and also a catalyst which catalyzes the hydrosilylation.

Preference is given to using, in the process according to the invention, the components specified above as preferred for the inventive enzyme preparations (SiH-functional polysiloxanes, polyethers bearing at least one terminally unsaturated group and polysiloxanes comprising terminal carbon-carbon double bonds).

In particular, the process can be performed in such a way that a hydrosilylation reaction is carried out in the presence of enzyme immobilizates which comprise enzymes or microorganisms comprising enzymes immobilized on an inert support. The polyether siloxane which forms in the hydrosilylation can provide the enzyme immobilizate with a polyethersiloxane coating.

The hydrosilylation can be carried out in a manner known to those skilled in the art. Preference is given to performing the hydrosilylation using the above-mentioned parameters/feedstocks/catalysts.

In a preferred embodiment of the process according to the invention, a particular amount of enzyme immobilizate is admixed with a mixture (reaction mixture) of the silicone reagents (compounds of the formulae (I), (II) and optionally (III) plus catalyst), for example by adding a mixture comprising compounds of the general formulae (I), (II) and optionally (III), and also Karstedt catalyst. For example, a mixture of compounds of the formulae (I), (II) and (III) in a molar mixing ratio of 1:0.6:0.6, and also Karstedt catalyst, for example 50 ppm based on the amount of silicone components present, can be added to 1 g of an enzyme immobilizate. For the purpose of optimizing the coating properties, it may be advantageous to dissolve the silicone components including the catalyst before the addition in a solvent, for example cyclohexane, toluene or another organic solvent, and then to add the solution to the enzyme immobilizate. When, for example, toluene is used as the solvent, it has been found to be advantageous, after adding the solution to the enzyme immobilizates, to disperse this mixture strongly for approx. 30 to 45 min, for example by means of a vortexer (Ika, level 9), until the bulk of the toluene has evaporated off. Subsequently, the resulting enzyme preparations are dried or hardened in a drying cabinet at 50° C., for example for 12 hours. Varying the mixing ratios of the compounds of the general formulae (I), (II) and optionally (III) allows the properties of the polyethersilicone coatings to be varied without any problem and matched to appropriate requirements.

A further embodiment of the process according to the invention differs from the aforementioned embodiment in that the enzyme immobilizates to be coated are immersed into the desired reaction mixture, then removed from the reaction mixture and dried. The removal can be effected, for example, using a screen which retains the enzyme immobilizate particles. The immersion time is preferably 1 to 10 minutes. The drying can be effected in a conventional drying cabinet. Preference is given to effecting the drying/hardening at a temperature of 20° C. to 80° C., preferably at 40° C. to 60° C., more preferably at approx. 50° C.

In a further embodiment of the process according to the invention, which is suitable especially for performance on the industrial scale, the hydrosilylation is carried out using a pelletizing pan unit (for example from Erweka or Eirich). In this case, a defined amount of enzyme immobilizate particles is added to the so-called pan unit and stirred. Subsequently, either the mixture comprising compounds of the formulae (I), (II) and optionally (III), and also catalyst and optionally solvent, is added, or else, preferably, a two-substance nozzle is used (for example from Schlick or others) to apply the mixture or the components under pressure (for example nitrogen or synthetic air) in the form of a fine mist of droplets, in order to ensure a very substantially homogeneous distribution on the particles. After a prolonged coating time, the particles are removed as described above and dried or hardened in a drying cabinet at a temperature of 20° C. to 80° C., preferably of 40° C. to 60° C., more preferably of 50° C., for several hours, and can then be stored at room temperature until further use.

In a further embodiment, the particles can be generated in a fluidized bed reactor (for example from Glatt), in which particles and the reaction mixture are applied in appropriate mixing ratios with strong dispersion. According to the invention, this can be carried out either in the so-called top-down method or in the so-called bottom-up method (also known as the Wurster method).

The inventive enzyme preparations can be used, for example, as biocatalysts, especially as industrial biocatalysts.

The examples which follow are intended to illustrate the present invention in detail without restricting the scope of protection which is evident from the description and the claims.

EXAMPLES

Materials and Methods

Novozym 435 (NZ435) is a commercial enzyme immobilizate from Novozymes A/S, Bagsvaerd, Denmark, specifically a lipase B from *C. antarctica* immobilized on a polymethacrylate by adsorption.

Hydrolytic Activity (Tributyrin Hydrolysis in Aqueous Medium):

The hydrolytic activity was determined by the so-called pH-stat method. In this method, the acid released in the hydrolysis is titrated against a base, such that the pH of the solution is kept constant. The time dependence of the consumption of base allows the acid released, and hence the enzyme activity, to be quantified. Illustrative procedure: 10 to 20 mg of catalytically active particles were added to 25 ml of Tris-HCl buffer (1 mM, pH 7.5; additionally contains 0.1 mM NaCl and $CaCl_2$) and 500 µl of tributyrin. The hydrolytic activity was quantified on an autotitrator (Tritroline alpha, from Schott) via the amount of base titrated in (50 mM NaOH).

Synthesis Activity in PLU Units (Propyl Laurate Synthesis Activity in Solvent-Free System):

10 mg of catalytically active particles were added to 5 ml of equimolar substrate solution (lauric acid and 1-propanol) and incubated while shaking and/or stirring at 60° C. Samples ($V_{sample}$: 50 µl) were taken every 5 min over 25 min and transferred into 950 µl of decane (internal standard: 4 mM dodecane). The PLUs were determined with reference to the initial product formation rates. Propyl laurate was detected by gas chromatography (retention time: 9.791 min) (Shimadzu 2010, BTX column from SGE; length 25 m, I.D. 0.22 µm; film: 0.25 µm; detector type: FID at 300° C.; injector temperature 275° C. and injection volume 1 µl, split ratio 35.0; carrier gas pressure (helium) 150 kPa; temperature programme: start temperature 60° C., hold for 1.5 min, temperature rise 20° C./min, end temperature 250° C., hold for 2.5 min).

Comparative Example 1

Determination of the Desorption Stability of Conventional Enzyme Immobilizates

For the purpose of determining the desorption stability of the particles under harsh reaction conditions, fractions of 20.0 mg of NZ435 were shaken (hereinafter, "incubated") in 20 ml of $MeCN/H_2O$ (1:1, v/v) solution at 45° C. for 30 min. The particles were recovered by means of a fluted filter and washed with 100 ml of $H_2O$, and dried at 50° C. for 12 h, in order to determine the hydrolytic activity and the synthesis activity in PLU according to the scheme described above and compare them with the results of native NZ435 from the batch used. For a representation which is more clearly understandable, the results can also be reported as a percentage with respect to the starting activity (hereinafter, "recovery rate"). The results can be taken from Table 1.

TABLE 1

Test results for comparative example 1:

| Enzymes | Synthesis act. before incubation [PLU/g] | Synthesis act. after incubation [PLU/g] (Recovery rate) | Hydrolytic activity before incubation [U/mg] | Hydrolytic activity after incubation [U/mg] (Recovery rate) |
|---|---|---|---|---|
| NZ435 native | 4400 | 147 (3.3%) | 1.54 | 0.10 (6.5%) |

Example 1

Preparation of a Stable Enzyme Preparation

Illustrative Preparation:

1 g of NZ435 particles were admixed in a metal dish with the reaction mixture consisting of various compositions of compounds of the general formulae (I), (II) and (III) (for composition see Table 2; the components of the general formulae (I) and (III) were prepared by processes familiar to those skilled in the art, as described, for example, in U.S. Pat. No. 7,196,153 B2, by equilibration; the monoallyl polyethers of the general formula (II) ($R^7$=methyl) were prepared by methods familiar to those skilled in the art, as described, for example, in EP 0427088 A2 or DE 2800710 A1, the diallyl polyethers of the general formula (II) ($R^7$=allyl) were purchased from Clariant, and Karstedt catalyst (Syloff 4000, product of Dow Corning, USA). The silicone components including the catalyst were each dissolved in 10 ml of toluene before the application and then added to the particles in the metal dish. After the addition, the mixture was immediately dispersed strongly by means of a vortexer (Ika, level 9) for 30 to 45 min, until the bulk of the toluene had evaporated off. Subsequently, the particles were dried at 50° C. in a drying cabinet for about 12 h. The results are shown in Table 2. The activities of the coated particles are both based on the unit of weight of coated particle and, for better comparability, based on the amount of native NZ435 used. Finally, the latter values are additionally shown in a percentage ratio relative to the activity of the native NZ435 (hereinafter "activity yield").

TABLE 2

Composition of the different coated particles

| No. | Starting weight of NZ435 | Component of the general formula (I); c = d = 0; $R^1$ = $R^{2a}$ = methyl, $R^{2b}$ = H | Component of the general formula (II); W = H; $R^5$ = —$CH_2$—; $R^6$ = methyl; | Component of the general formula (III); b = c = d = 0; $R^3$ = methyl, $R^4$ = vinyl | Proportion of NZ435 [%] | Hydrolysis act. [U/mg of immob. (U/mg of NZ435; activity yield)] | Synthesis act. [PLU/g of immob. (PLU/g of NZ435; activity yield)] |
|---|---|---|---|---|---|---|---|
| NZ435[1] | 1 g | — | — | — | 100 | 1.54 | 4400 (4400) |
| i | 1 g | a = 43, b = 5 490 mg | $x_1$ = 25, $x_2$ = $y_1$ = $y_2$ = z = 0, $R^7$ = allyl; 71.4 mgL | a = 98 438.6 mg | 50 | 0.50 (1.00; 65%) | 1803 (3606; 82%) |
| ii | 1 g | a = 43, b = 5 735 mg | $x_1$ = 25, $x_2$ = $y_1$ = $y_2$ = z = 0, $R^7$ = allyl; 107.1 mg | a = 98 657.9 mg | 40 | 0.48 (1.20; 78%) | 1504 (3759; 85%) |
| iii | 1 g | a = 43, b = 5 514.1 mg | $x_1$ = 25, $x_2$ = $y_1$ = $y_2$ = z = 0, $R^7$ = allyl; 38.9 mg | a = 98 447 mg | 50 | 0.47 (0.94; 55%) | 1767 (3534; 80%) |
| iv | 1 g | a = 43, b = 5 771.3 mg | $x_1$ = 25, $x_2$ = $y_1$ = $y_2$ = z = 0, $R^7$ = allyl; 58.4 mg | a = 98 670.2 mg | 40 | 0.39 (0.98; 64%) | 1592 (3980; 90%) |
| v | 2 g | a = 43, b = 5 450 mg | $x_1$ = 23, $y_1$ = 5, $x_2$ = $y_2$ = z = 0, $R^7$ = methyl; 190 mg | a = 98 2360 mg | 40 | 0.47 (1.20; 78%) | 1540 (3850; 88%) |
| vi | 2 g | a = 43, b = 5 470 mg | $x_1$ = 23, $y_1$ = 5, $x_2$ = $y_2$ = z = 0, $R^7$ = methyl; 100 mg | a = 98 2430 mg | 40 | 0.47 (1.20; 78%) | 1875 (4687; 106%) |
| vii | 2 g | a = 43, b = 5 420 mg | $x_1$ = $x_2$ = 2, $y_1$ = $y_2$ = 8, z = 15, $R^7$ = allyl; 340 mg | a = 98 2240 mg | 40 | 0.41 (1.03; 67%) | 1771 (4428; 100%) |
| viii | 2 g | a = 43, b = 5 410 mg | $x_1$ = $x_2$ = 2, $y_1$ = $y_2$ = 8, z = 15, $R^7$ = allyl; 390 mg | a = 98 2200 mg | 40 | 0.36 (0.90; 58%) | 1710 (4275; 97%) |

[1]Data for native NZ435 taken from Comparative Example 1

The particles prepared by this process have, compared to the untreated immobilizate, activity yields in the hydrolysis of 55% up to 78% (Example 1 i, 1.20 U/mg of NZ435 compared to 1.54 U/mg for untreated NZ435, as described in Comparative Example 1). In the synthesis, very good activity yields of 80% up to 106% were achievable.

Example 2

Determination of the Desorption Stability of Stable Enzyme Preparations

Analogously to Comparative Example 1, the particles obtained from Example 1 were treated with water/acetonitrile and then the hydrolysis activity and the synthesis activity based on the proportion by weight of NZ435 in the preparation were determined. The result of this determination can be taken from Table 3; analogously to Comparative Example 1, the recovery rate was also determined.

TABLE 3

Results from Example 2

| | Proportion of NZ435 [%] | Hydrolysis act. before incubation [U/mg of NZ435] | Hydrolysis act. after incubation [U/mg of NZ435]; (recovery rate) | Synthesis act. before incubation [U/mg of NZ435] | Synthesis act. after incubation [U/mg of NZ435]; (recovery rate) |
|---|---|---|---|---|---|
| NZ435[1] | 100 | 1.54 | 0.10; (6.5%) | 3761 | 147; (3.9%) |
| i | 50 | 1.00 | 0.38; (38%) | 3606 | 340; (9.4%) |
| ii | 40 | 1.20 | 0.81; (68%) | 3759 | 2402; (64%) |
| iii | 50 | 0.94 | 0.28; (30%) | 3534 | 240; (6.8%) |
| iv | 40 | 0.98 | 0.58; (59%) | 3980 | 1500; (33%) |
| v | 40 | 1.20 | 0.38; (32%) | 3850 | 425; (11%) |
| vi | 40 | 1.20 | 0.43; (36%) | 4587 | 875; (19%) |
| vii | 40 | 1.03 | 0.50; (51%) | 4428 | 603; (14%) |
| viii | 40 | 0.90 | 0.55; (61%) | 4275 | 695; (16%) |

[1]Data for native NZ435 taken from Comparative Example 1

Whereas untreated native enzyme immobilizate after incubation exhibits almost no hydrolysis or synthesis activity whatsoever, the polyethersiloxane-coated particles exhibit hydrolysis activities of up to 68% of the starting activity and synthesis activities of up to 64% of the starting activity.

While the present invention has been particularly shown and described with respect to preferred embodiments thereof,

What is claimed is:

1. An enzyme preparation comprising:
   an enzyme immobilizate including microorganisms comprising enzymes immobilized on an inert support; and
   a polyethersiloxane coating located on said enzyme immobilizate, said polyethersiloxane coating is obtained by hydrosilylating Si—H-functional polysiloxanes, in which the olefinic units used are polyethers bearing at least one terminally unsaturated group, with the proviso that at least one of the polyether groups has at least two terminally unsaturated groups.

2. The enzyme preparation according to claim 1, wherein said enzymes are hydrolases.

3. The enzyme preparation according to claim 1, wherein the inert support has a particle size distribution in which 90% of the particles have a particle size of 10 to 5000 µm.

4. The enzyme preparation according to claim 1, wherein the inert support is silica, polyvinylstyrene, polymethacrylate or polyacrylate.

5. The enzyme preparation according to claim 1, wherein the Si—H-functional polysiloxanes are Si—H polysiloxanes of formula (I)

$$M_a D_b D'_c T_d Q_e \quad (I)$$

where
   $M=[R^1_2 R^{2a} SiO_{1/2}]$
   $D=[R^1_2 SiO_{2/2}]$
   $D'=[R^1 R^{2b} SiO_{2/2}]$
   $T=[R^1 SiO_{3/2}]$
   $Q=[SiO_{4/2}]$
   $a+b+c+d+e=3$ to 850,
   $a=2$ to 10,
   $b=1$ to 800,
   $c=0$ to 400,
   $d=0$ to 10,
   $e=0$ to 10,
   $R^1$ are the same or different and are each independently selected from saturated or unsaturated, optionally branched alkyl groups having 1 to 30 carbon atoms, alkaryl radicals having 7 to 30 carbon atoms, or aryl radicals having 6 to 30 carbon atoms,
   $R^{2a}$ is independently hydrogen or $R^1$ and
   $R^{2b}$ is independently hydrogen or $R^1$.

6. The enzyme preparations according to claim 5, wherein
   $a+b+c+d+e=6$ to 160,
   $a=2$,
   $b=2$ to 150,
   $c=2$ to 75,
   $d=0$ and
   $e=0$.

7. The enzyme preparation according to claim 1, wherein the polyethers bearing at least one terminally unsaturated group are those of formula (II):

(II)

where
   $x_1+x_2+y_1+y_2=1$ to 500,
   $x_1=0$ to 200,
   $x_2=0$ to 100,
   $y_1=0$ to 200,
   $y_2=0$ to 100,
   $z=0$ to 500,
   W=hydrogen or methyl,
   $R^5$ is an optionally branched, optionally substituted alkylene radical which optionally bears double bonds and has 1 to 30 carbon atoms,
   $R^6$ is independently a radical selected from methyl, ethyl or phenyl, and
   $R^7$ is an optionally branched, optionally substituted alkyl radical or carboxyl radical which optionally contains double bonds and has 1 to 30 carbon atoms, with the proviso that, when $z=0$, $x_2=y_2=0$.

8. The enzyme preparation according to claim 1, wherein said olefinic units used further include polysiloxanes which bear terminally unsaturated organic radicals, and wherein the polysiloxanes which bear terminally unsaturated organic radicals are of formula (III)

$$M_m D_n D'_o T_p Q_q \quad (III)$$

where
   $M=[R^3_2 R^4 SiO_{1/2}]$
   $D=[R^3_2 SiO_{2/2}]$
   $D'=[R^3 R^4 SiO_{2/2}]$
   $T=[R^3 SiO_{3/2}]$
   $Q=[SiO_{4/2}]$
   $m+n+o+p+q=3$ to 1000,
   $m=2$ to 10,
   $n=1$ to 800,
   $o=0$ to 20,
   $p=0$ to 10,
   $q=0$ to 10,
   $R^3$ are the same or different and are each independently selected from saturated or unsaturated, optionally branched alkyl groups having 1 to 30 carbon atoms, alkaryl radicals having 7 to 30 carbon atoms, or aryl radicals having 6 to 30 carbon atoms, and
   $R^4$ is independently a terminally unsaturated alkyl radical, preferably vinyl, or an alkoxy radical or $R_3$.

9. The enzyme preparation according to claim 8, wherein
   $m+n+o+p+q=10$ to 600,
   $m=2$,
   $n=2$ to 600,
   $o=0$,
   $p=0$,
   $q=0$, and
   $R^4$ is independently a terminally unsaturated alkyl radical.

10. An enzyme preparation comprising:
    an enzyme immobilizate including microorganisms comprising enzymes immobilized on an inert support; and a polyethersiloxane coating located on said enzyme immobilizate, said polyethersiloxane coating is obtained by hydrosilylating Si—H-functional polysiloxanes, in which the olefinic units used are polyethers bearing at least one terminally unsaturated group and siloxanes which bear unsaturated organic radicals, with the proviso that at least one olefinic unit of at least one of said polyethers and/or said siloxanes has at least two terminally unsaturated groups.

11. The enzyme preparation according to claim 10, wherein the Si—H-functional polysiloxanes are Si—H polysiloxanes of formula (I)

$$M_a D_b D'_c T_d Q_e \quad (I)$$

where
$M=[R^1{}_2 R^{2a} SiO_{1/2}]$
$D=[R^1{}_2 SiO_{2/2}]$
$D'=[R^1 R^{2b} SiO_{2/2}]$
$T=[R^1 SiO_{3/2}]$
$Q=[SiO_{4/2}]$
$a+b+c+d+e=3$ to 850,
$a=2$ to 10,
$b=1$ to 800,
$c=0$ to 400,
$d=0$ to 10,
$e=0$ to 10,
$R^1$ are the same or different and are each independently selected from saturated or unsaturated, optionally branched alkyl groups having 1 to 30 carbon atoms, alkaryl radicals having 7 to 30 carbon atoms, or aryl radicals having 6 to 30 carbon atoms,
$R^{2a}$ is independently hydrogen or $R^1$ and
$R^{2b}$ is independently hydrogen or $R^1$.

12. The enzyme preparations according to claim 11, wherein
$a+b+c+d+e=6$ to 160,
$a=2$,
$b=2$ to 150,
$c=2$ to 75,
$d=0$ and
$e=0$.

13. The enzyme preparation according to claim 10, wherein the polyethers bearing at least one terminally unsaturated group are those of formula (II):

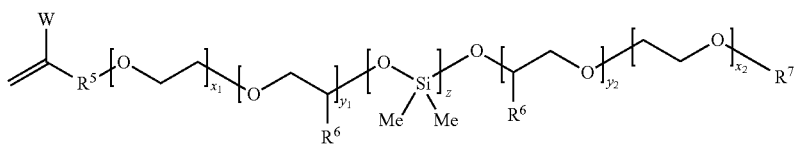

where
$x_1+x_2+y_1+y_2=1$ to 500,
$x_1=0$ to 200,
$x_2=0$ to 100,
$y_1=0$ to 200,
$y_2=0$ to 100,
$z=0$ to 500,
W=hydrogen or methyl,
$R^5$ is an optionally branched, optionally substituted alkylene radical which optionally bears double bonds and has 1 to 30 carbon atoms,
$R^6$ is independently a radical selected from methyl, ethyl or phenyl, and $R^7$ is an optionally branched, optionally substituted alkyl radical or carboxyl radical which optionally contains double bonds and has 1 to 30 carbon atoms, with the proviso that, when $z=0$, $x_2=y_2=0$.

14. The enzyme preparation according to claim 10, wherein said siloxanes which bear unsaturated organic radicals, and wherein the polysiloxanes which bear terminally unsaturated organic radicals are of formula (III)

$$M_m D_n D'_o T_p Q_q \quad (III)$$

where
$M=[R^3{}_2 R^4 SiO_{1/2}]$
$D=[R^3{}_2 SiO_{2/2}]$
$D'=[R^3 R^4 SiO_{2/2}]$
$T=[R^3 SiO_{3/2}]$
$Q=[SiO_{4/2}]$
$N^2=m+n+o+p+q=3$ to 1000,
$m=2$ to 10,
$n=1$ to 800,
$o=0$ to 20,
$p=0$ to 10,
$q=0$ to 10,
$R^3$ are the same or different and are each independently selected from saturated or unsaturated, optionally branched alkyl groups having 1 to 30 carbon atoms, alkaryl radicals having 7 to 30 carbon atoms, or aryl radicals having 6 to 30 carbon atoms, and
$R^4$ is independently a terminally unsaturated alkyl radical, preferably vinyl, or an alkoxy radical or $R_3$.

15. The enzyme preparation according to claim 14, wherein
$m+n+o+p+q=10$ to 600,
$m=2$,
$n=2$ to 600,
$o=0$,
$p=0$,
$q=0$ and
$R^4$ is independently a terminally unsaturated alkyl radical.

16. A process for preparing an enzyme preparation, comprising coating an enzyme immobilizate which comprises microorganisms comprising enzymes immobilized on an inert support with a polyethersiloxane coating, said polyethersiloxane coating is obtained by hydrosilylating Si—H-functional polysiloxanes, in which the olefinic units used are polyethers bearing at least one terminally unsaturated group and optionally additionally siloxanes which bear terminally unsaturated organic radicals, with the proviso that at least one olefinic unit which has at least two terminally unsaturated groups is present.

17. The process according to claim 16, wherein the enzyme immobilizates are provided with a polyethersilicone coating by contacting the enzyme immobilizates, under hydrosilylation conditions, with a reaction mixture which comprises Si—H-functional polysiloxanes, polyethers bearing at least one terminally unsaturated group, optionally polysiloxanes containing terminal carbon-carbon double bonds, and also a catalyst which catalyses the hydrosilylation.

* * * * *